(12) United States Patent
Meyer et al.

(10) Patent No.: US 11,504,074 B1
(45) Date of Patent: Nov. 22, 2022

(54) METHOD AND SYSTEM FOR AUTOMATICALLY REQUESTING MEDICAL ASSISTANCE

(71) Applicant: UIPCO, LLC, San Antonio, TX (US)

(72) Inventors: Gregory Brian Meyer, San Antonio, TX (US); Mark Anthony Lopez, Helotes, TX (US); Ravi Durairaj, San Antonio, TX (US); Nolan Serrao, Plano, TX (US); Victor Kwak, Frisco, TX (US); Ryan Thomas Russell, The Colony, TX (US); Christopher Russell, The Colony, TX (US); Ruthie D. Lyle, Durham, NC (US)

(73) Assignee: United Services Automobile Association (USAA), San Antonio, TX (US)

( * ) Notice: Subject to any disclaimer, the term of this patent is extended or adjusted under 35 U.S.C. 154(b) by 0 days.

(21) Appl. No.: 16/942,838

(22) Filed: Jul. 30, 2020

Related U.S. Application Data

(60) Provisional application No. 62/880,720, filed on Jul. 31, 2019.

(51) Int. Cl.
*A61B 5/00* (2006.01)
*G08B 21/04* (2006.01)
*A61B 5/145* (2006.01)

(52) U.S. Cl.
CPC ............ *A61B 5/747* (2013.01); *A61B 5/0004* (2013.01); *A61B 5/0022* (2013.01);
(Continued)

(58) Field of Classification Search
CPC ........ A61B 5/0015; A61B 5/002–0022; A61B 5/746–747; A61B 5/0004; A61B 5/0024; A61B 5/14532; A61B 5/14546; A61B 5/1112; A61B 5/681; A61B 5/7264–7267; A61B 5/7275; A61B 5/7282;
(Continued)

(56) References Cited

U.S. PATENT DOCUMENTS 6,292,687 B1 * 9/2001 Lowell ................... A61B 5/002
                                                600/515
9,852,599 B1 * 12/2017 Slavin .................... A61B 5/443
(Continued)

FOREIGN PATENT DOCUMENTS

CN         109686448 A  *  4/2019

OTHER PUBLICATIONS

Machine Translation of CN 109686448A (Year: 2022).*

*Primary Examiner* — Eric F Winakur
*Assistant Examiner* — Alice Ling Zou
(74) *Attorney, Agent, or Firm* — Plumsea Law Group, LLC

(57) ABSTRACT

A system and method for automatically requesting assistance for a user experiencing a medical emergency is disclosed. The system includes a user device with a sensor to detect sensed information. Based on the sensed information the user device can determine if the user is experiencing a medical emergency. The user device can communicate with nearby devices over one or more networks and send information about the medical emergency to the nearby devices. The information can include the type of medical emergency, the location of the user experiencing the medical emergency, and any instructions for providing the user with assistance.

19 Claims, 8 Drawing Sheets

(52) U.S. Cl.
CPC .......... *A61B 5/14532* (2013.01); *A61B 5/681* (2013.01); *A61B 5/746* (2013.01); *G08B 21/0453* (2013.01)

(58) Field of Classification Search
CPC ...... A61B 5/7465–747; G08B 21/0453; G08B 21/0446; G08B 21/0492; G08B 21/088; G08B 21/043–0461; G08B 25/00–005; G08B 25/014–016; G08B 29/186; G16H 40/60; G16H 40/63; G16H 40/67; G16H 50/20; G16H 50/30; G16H 80/00; H04W 4/38; H04W 4/029; H04W 4/025; H04W 4/024
See application file for complete search history.

(56) References Cited

U.S. PATENT DOCUMENTS

| | | | |
|---|---|---|---|
| 2003/0128125 A1* | 7/2003 | Burbank | A61M 60/515 340/521 |
| 2004/0102931 A1* | 5/2004 | Ellis | H04W 4/029 702/188 |
| 2005/0153681 A1* | 7/2005 | Hanson | H04W 76/50 455/456.1 |
| 2008/0139898 A1* | 6/2008 | Johnson | A61B 5/0002 600/301 |
| 2014/0118140 A1* | 5/2014 | Amis | G08B 25/08 340/539.13 |
| 2014/0191863 A1* | 7/2014 | Ten Kate | A61B 5/7203 340/539.12 |
| 2015/0269824 A1* | 9/2015 | Zhang | A61B 5/746 340/539.12 |

* cited by examiner

METHOD AND SYSTEM FOR AUTOMATICALLY REQUESTING MEDICAL ASSISTANCE

CROSS-REFERENCE TO RELATED APPLICATIONS

This application claims the benefit of Provisional Patent Application No. 62/880,720 filed Jul. 31, 2019, and titled "Method and System for Automatically Requesting Medical Assistance," which is incorporated by reference herein in its entirety.

TECHNICAL FIELD

The present disclosure generally relates to methods and systems for requesting medical assistance, and in particular to sending requests for medical assistance to nearby devices.

BACKGROUND

Many phones and wearable devices are able to sense information about a user's current health. For example, some wearable devices include sensors that can detect irregular heart rhythms. However, these devices lack provisions for helping obtain assistance for the user after a problematic health condition has been detected. In some situations a user is unable to contact emergency services. Even when the user or a bystander are able to contact emergency services, the user often has to wait a significant period of time for the emergency services personnel to arrive and begin assisting the user. Even a delay of just a few minutes in receiving emergency services can mean the difference between life or death, or can result in a diminished quality of life.

There is a need in the art for a system and method that addresses the shortcomings discussed above.

SUMMARY

In one aspect, a method of requesting assistance for a user experiencing a medical emergency includes steps of receiving sensed information from a sensor disposed in a user device associated with the user, determining that the user is experiencing a medical emergency based on the sensed information, establishing communication with one or more nearby devices, and automatically sending information associated with the medical emergency to the one or more nearby devices.

In another aspect, a method of requesting assistance for a user experiencing a medical emergency includes steps of determining that a user is experiencing a medical emergency, establishing communication with a nearby device, retrieving a location for the nearby device, determining a route between the user and the nearby device, calculating a route length for the route, retrieving a predetermined distance, and sending information about the medical emergency to the nearby device if the route length is less than or equal to the predetermined distance.

In another aspect, a user device includes a sensor, a navigation system, and a communication system. The user device determines if a user associated with the user device is experiencing a medical emergency based on sensed information detected by the sensor. The user device establishes communication with a nearby device using the communication system, and the user device receives a location from the nearby device. The user device determines a navigation route between the user device and the location of the nearby device using the navigation system. The user device sends information about the medical emergency to the nearby device when the navigation route is less than a predetermined distance.

Other systems, methods, features, and advantages of the disclosure will be, or will become, apparent to one of ordinary skill in the art upon examination of the following figures and detailed description. It is intended that all such additional systems, methods, features, and advantages be included within this description and this summary, be within the scope of the disclosure, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like reference numerals designate corresponding parts throughout the different views.

DESCRIPTION OF THE EMBODIMENTS

A system and method for requesting medical assistance for a user by sending information to nearby devices is disclosed. The system includes a device, such as a wearable device, that can sense information about a user. The system can determine, based on the sensed information, if the user has experienced a medical emergency, such as a heart attack. The system can then broadcast a message to other nearby devices over one or more networks. The message may explain that a medical emergency has occurred, request assistance for the user, as well as provide the location of the user. The same message or a follow-up message could also include instructions for assisting the user. The system may simultaneously automatically contact emergency services and check to see if the user has been assisted by another user with a nearby device and/or emergency services personnel. In some cases, the system could automatically send messages to friends, family and/or an emergency contact to request assistance. Additionally, in some cases, information about the medical emergency could be sent to a medical provider. Here, a medical provider may include an ambulance driver, a doctor, and/or a hospital.

The system is able to identify problematic health conditions and emergencies in real time so that emergency services can be immediately requested. The system is also able to leverage any networks that the user's device is connected to in order to request assistance for the user from people who may be able to get to the user before the emergency services arrive. In some cases, reducing the amount of time that a user has to wait for assistance may improve medical outcomes.

Figure 1:
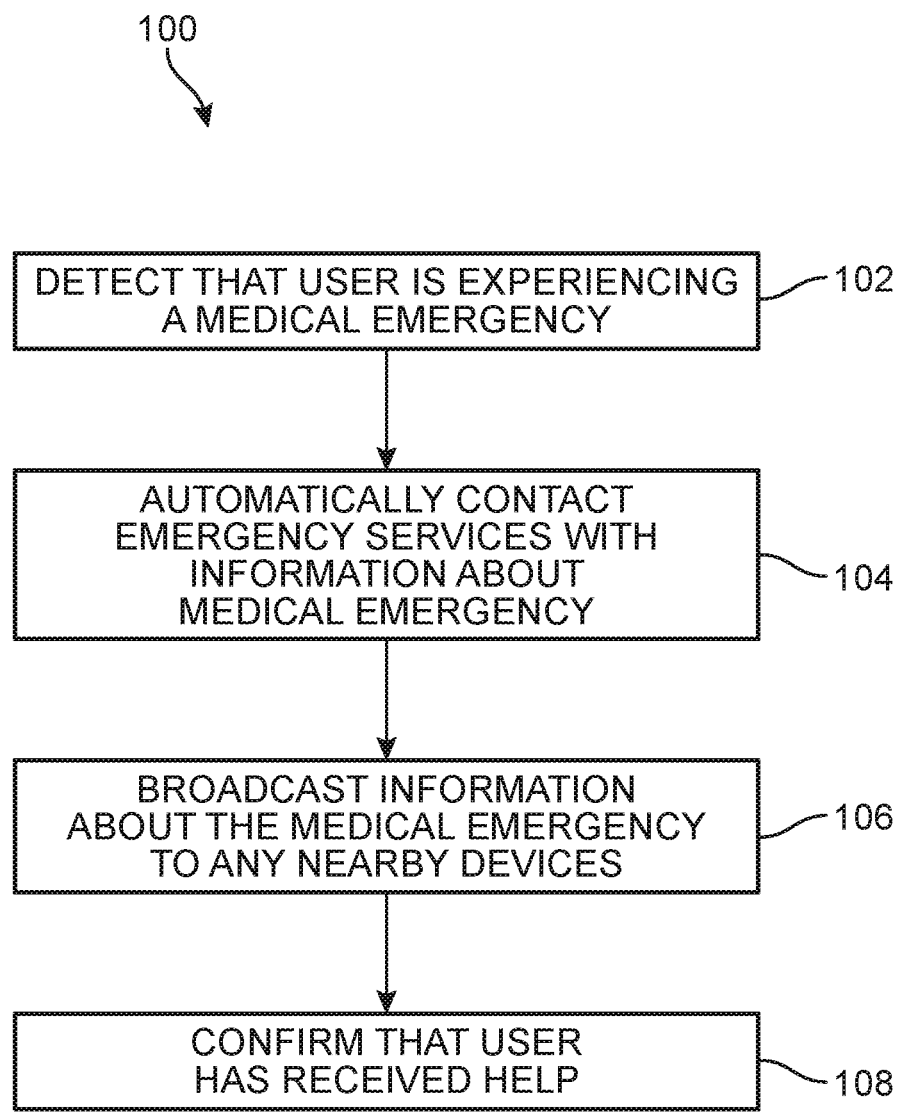
FIG. 1 is a schematic view of a method of automatically sending information about a medical emergency to nearby devices in order to facilitate helping a user, according to an embodiment.

FIG. 1 is a schematic view of a process 100 for automatically sending information about a medical emergency to nearby devices in order to facilitate helping a user as quickly as possible. For clarity, the present disclosure uses the term "assisted user" to refer to a user requiring and/or actively receiving assistance, such as medical assistance. The present disclosure also uses the term "assisting user" to refer to a user providing (or possibly providing) assistance, such as medical assistance. Thus, a person who has experienced a heart attack and requires medical attention may be referred to as the assisted user, and a nearby person who comes over to help the assisted user may be referred to as an assisting user.

Starting in step 102, a user's device (for example, a phone or smart watch) could detect that the user is experiencing a medical emergency. Examples of such devices are listed below and shown in FIG. 2. As used herein, the term "medical emergency" refers to any medical condition requiring immediate medical assistance or attention. For example, a user experiencing a heart attack may be in immediate need of a defibrillator and/or CPR. As another example, a user who has nearly drowned in a pool may be in need of CPR. As yet another example, a user experiencing hypoglycemia may be in need of an immediate source of food that is high in carbohydrates.

Next, in an optional step 104, the user's device may automatically contact emergency services with information about the medical emergency. In some cases, the user device could automatically dial emergency services (for example, dial 911) so that the user could speak with an emergency services operator. However, in other cases, the user device could send messages (via SMS or other protocols) to an emergency dispatch service, especially if the user is unable to talk or otherwise communicate. If the device is not able to send messages directly to an emergency dispatch service, the user device could call the dispatch service and provide the type of emergency and location of the user as spoken speech. In some cases, this could be enabled using any built-in natural language processing modules.

In step 106, the user's device may broadcast (or otherwise send) information about the medical emergency to any nearby devices. As used herein, the term "nearby devices" refers to devices within some predetermined distance of the user's device. The choice of predetermined distance can vary according to the context, and could generally range from a distance of a few meters to one or more miles. In the context of medical emergencies, the predetermined distance could be dynamically selected according to how urgently a user needs assistance. In some cases, information about the emergency may also be transmitted specifically to caregivers of the person experiencing the emergency, whose contact information may be retrieved by the user's phone, for example. A caregiver may be a family member or medical professional familiar with the person experiencing the medical emergency. Priority may be given to caregivers who are closest to the person. In some cases, while messages may be broadcast only to users within a predetermined range of the user, messages may be sent to caregivers even if they fall outside of that predetermined range.

In step 108, the user's device can confirm that the user has received help. Specifically, the user's device can confirm that the user has received help from an owner of a nearby device (that is, an assisting user) and/or that the user has received help from emergency services personnel.

Figure 2:
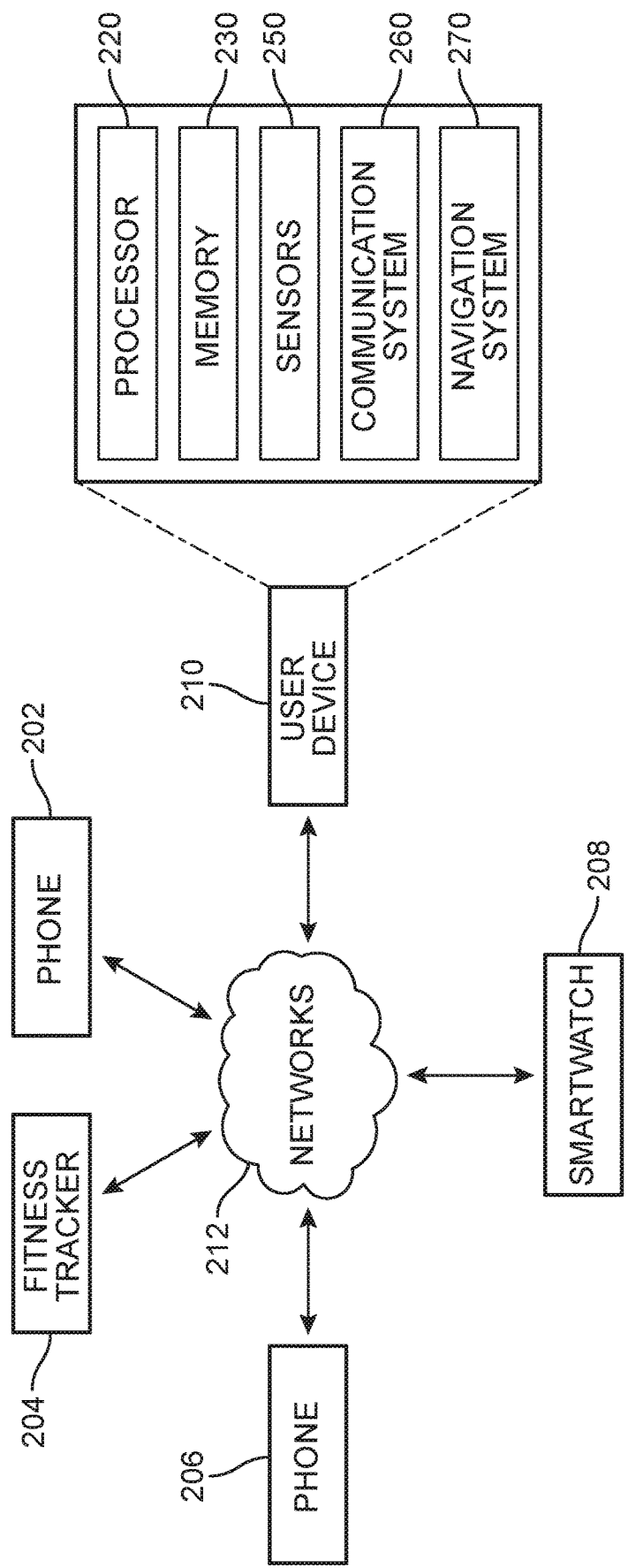
FIG. 2 is a schematic view of a plurality of networked devices, according to an embodiment.

FIG. 2 is a schematic view of a plurality of devices connected over one or more networks 212 to a user device 210. Exemplary devices may include, but are not limited to: mobile phones, tablets, smart watches, fitness trackers and other wearable devices. As examples, a first mobile phone 202, a fitness tracker 204, a second mobile phone 206, and a smartwatch (or wristband) 208 may be connected to user device 210 over networks 212. Each of these devices may generally be worn and/or carried by a user.

Generally, networks 212 could comprise any kinds of networks or other communication channels. Networks 212 could include one or more Wide Area Networks (WANs), Local Area Networks (LANs), Wi-Fi networks, Bluetooth or other Personal Area Networks, cellular networks, as well as other kinds of networks. It may be appreciated that different devices could communicate using different networks and/or communication protocols.

User device 210 could be any kind of device, including a mobile phone, a smart watch, a fitness tracker, or another type of wearable. In some embodiments, user device 210 could include one or more embedded sensors that are implanted within a user. For example, implantable inductor-capacitor sensors could be used to measure forces, pressures, temperatures, electrical signals, and/or other biological parameters in the body. In one embodiment, user device 210 is a smart watch. User device 210 may include provisions for communicating with, and processing information from, nearby devices. Moreover, the other devices communicating with user device 210 may also include some or all of these provisions.

As seen in FIG. 2, user device 210 may include one or more processors 220 and memory 230. Memory 230 may comprise a non-transitory computer readable medium. Instructions stored within memory 230 may be executed by the one or more processors 220. User device 210 may also include one or more sensors 250, a communication system 260, and a navigation system 270.

Communication system 260 may include radios or other provisions for communicating using one or more communication methods. In particular, communication system 260 includes provisions for communicating with other nearby devices over networks 212. For example, each communication system could include a Wi-Fi radio, a Bluetooth radio, and/or a cellular network radio.

Navigation system 270 may comprise any system capable of providing directions and/or other kinds of routing information between two or more locations. In some cases, navigation system 270 can provide directions in an outdoor environment. In other cases, navigation system 270 can provide directions in an indoor environment. In some cases, navigation system 270 may provide directions in both outdoor and indoor environments.

Figure 3:
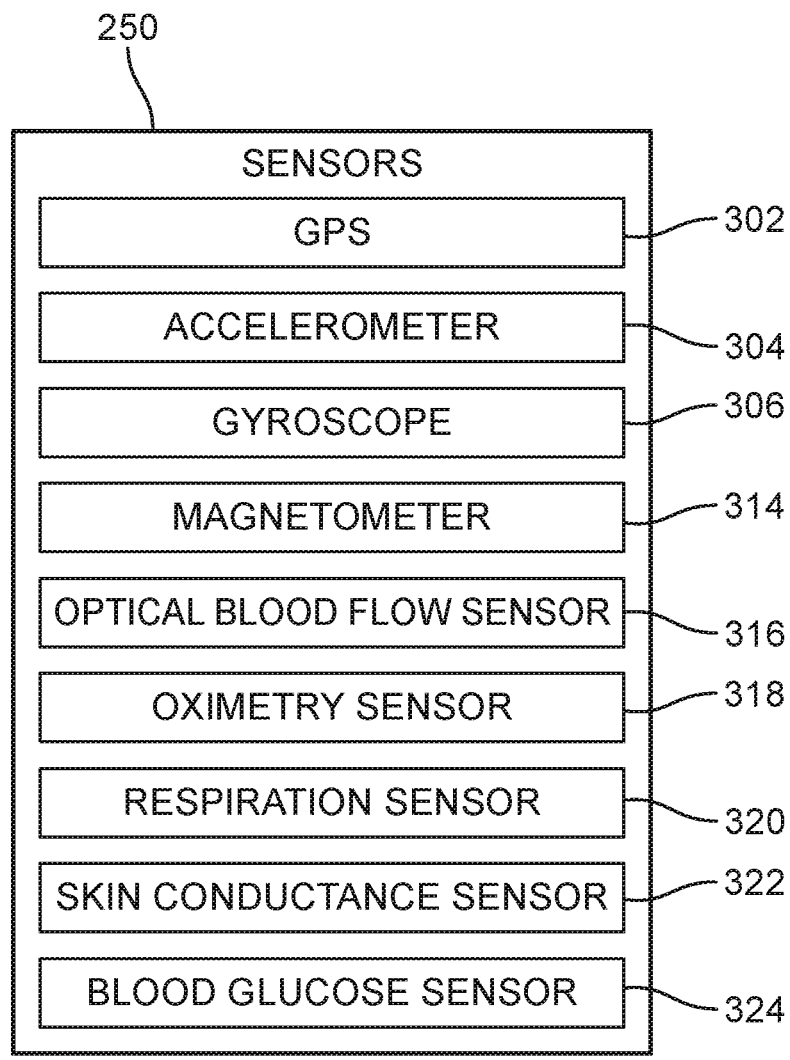
FIG. 3 is a schematic view of a set of sensors, according to an embodiment.

As seen in FIG. 3, a user device can include one or more sensors 250 that are used in mobile phones, smart watches, fitness trackers, implantable sensors, or other wearable devices. These may include a GPS receiver 302, an accelerometer 304, a gyroscope 306, a magnetometer 314, an optical blood flow sensor 316 (to detect heart rate), an oximetry sensor 318 (to detect blood oxygen levels), a respiration sensor 320 and a skin conductance sensor 322. In some cases, a respiration sensor could be a radar-based sensor capable of detecting very small movements, such as the rise and fall of a user's chest. Some embodiments may also include a blood glucose sensor 324 that may provide continuous blood glucose testing.

Figure 4:
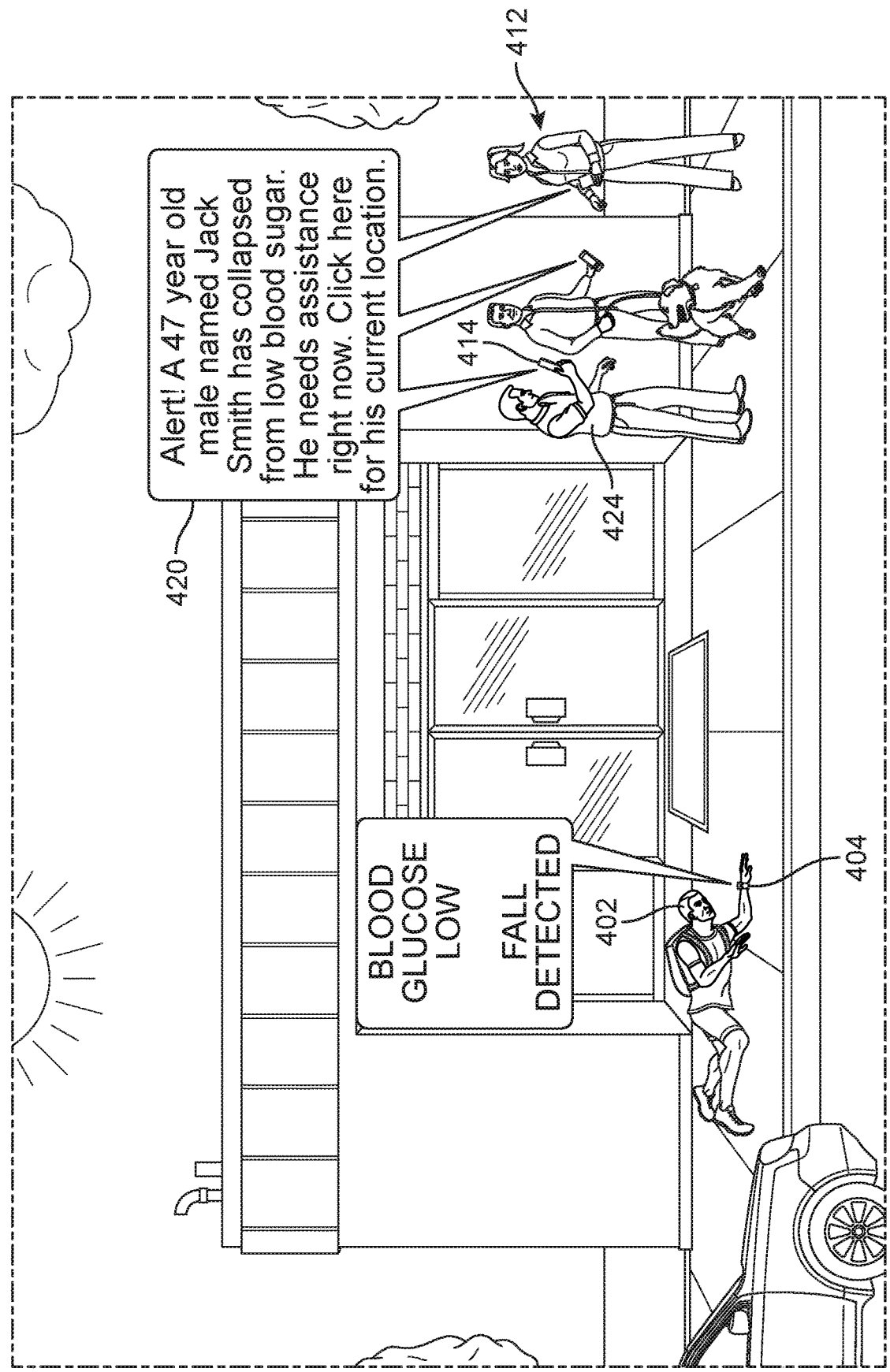
FIG. 4 is a schematic view of a scenario where a person has collapsed on the ground and a message is automatically broadcast to other users on a local network, according to an embodiment.
Figure 5:
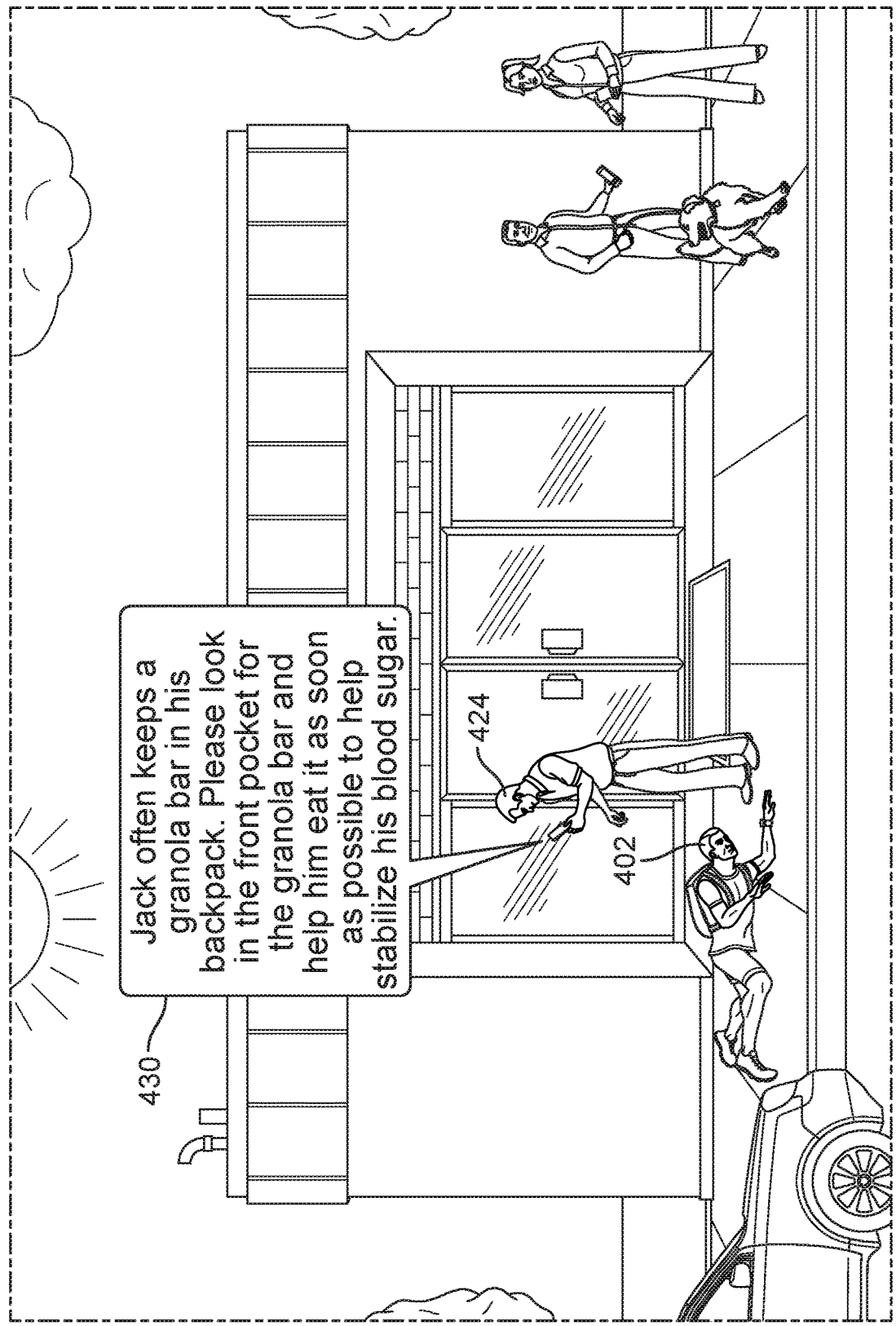
FIG. 5 is a schematic view of the scenario in FIG. 4, in which specific instructions for assisting the person are automatically transmitted to another user's device.

FIGS. 4 and 5 depicts schematic views of a scenario in which the present system and method may be used to provide assistance to a user experiencing a medical emergency. In FIG. 4, a user 402 (the "assisted user") is experiencing hypoglycemia (severely low blood sugar) and has collapsed on the ground. The user's device 404 (a smart watch) detects that the user is hypoglycemic (via blood glucose sensor 324, for example) and that the user has fallen (via accelerometer 324, for example). Device 404 then determines that the user is having a medical emergency and is in need of assistance. In some cases, device 404 may automatically call emergency services (e.g., 911) so long as device 404 has access to a cellular network or other network infrastructure for contacting emergency services. In addition, in some cases, device 404 may broadcast information about the medical emergency as well as location information to nearby devices associated with nearby users 412. For example, in FIG. 4, a message 420 is sent by device 404 and received at a nearby device 414. The message informs the device's user that user 402 (Jack Smith) has collapsed from low blood sugar and is in need of assistance. The message also provides a way for user 424 of nearby device 414 to obtain location information for user 402.

In FIG. 5, assisting user 424 has moved next to assisted user 424. Assisted user 424 receives an additional message 430 with instructions for assisting user 424. Specifically, user 424 is told to locate a granola bar in a backpack worn by user 402 and to help user 402 eat the granola bar.

Figure 6:
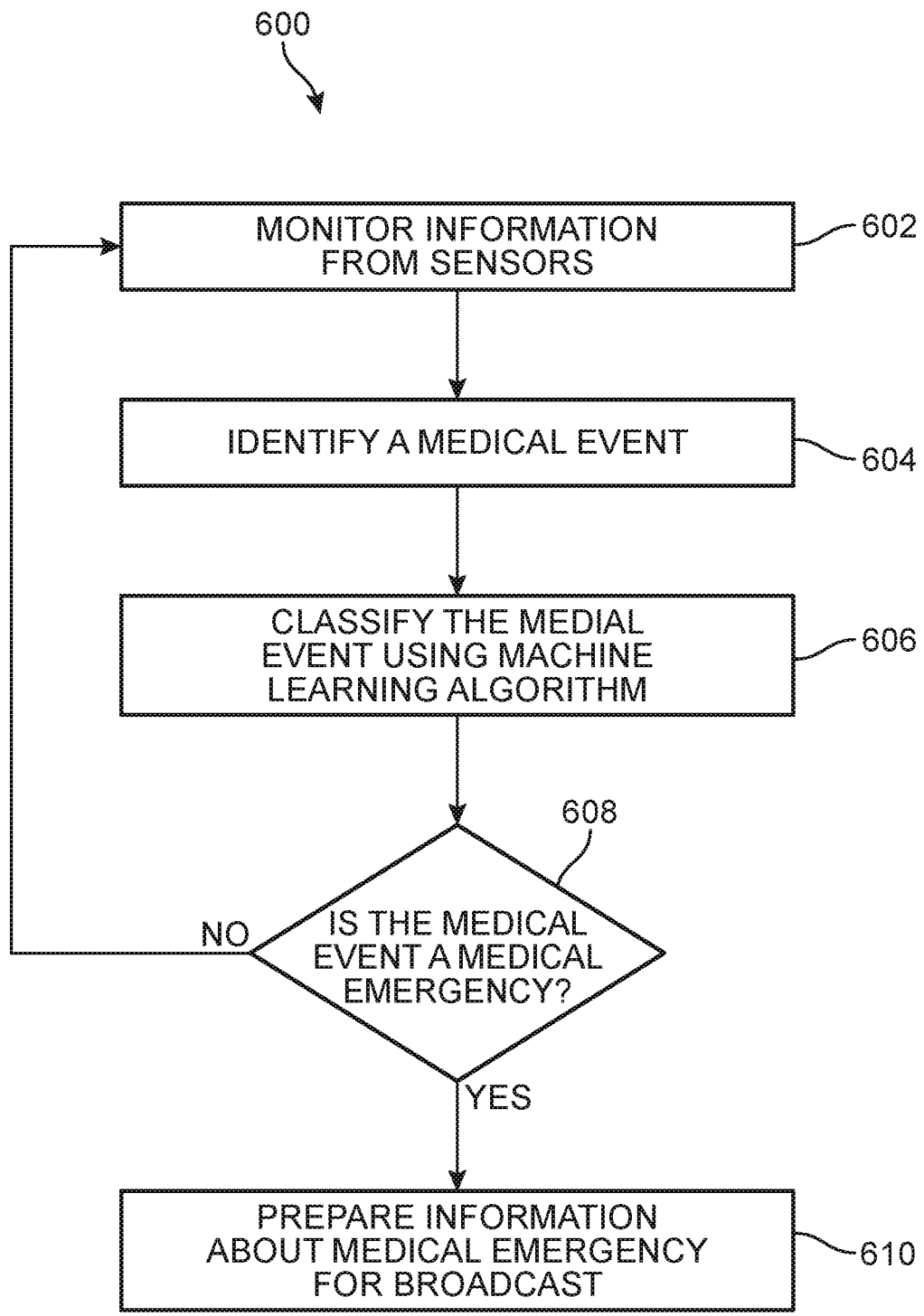
FIG. 6 is a schematic view of a method for detecting a medical emergency, according to an embodiment.
Figure 7:
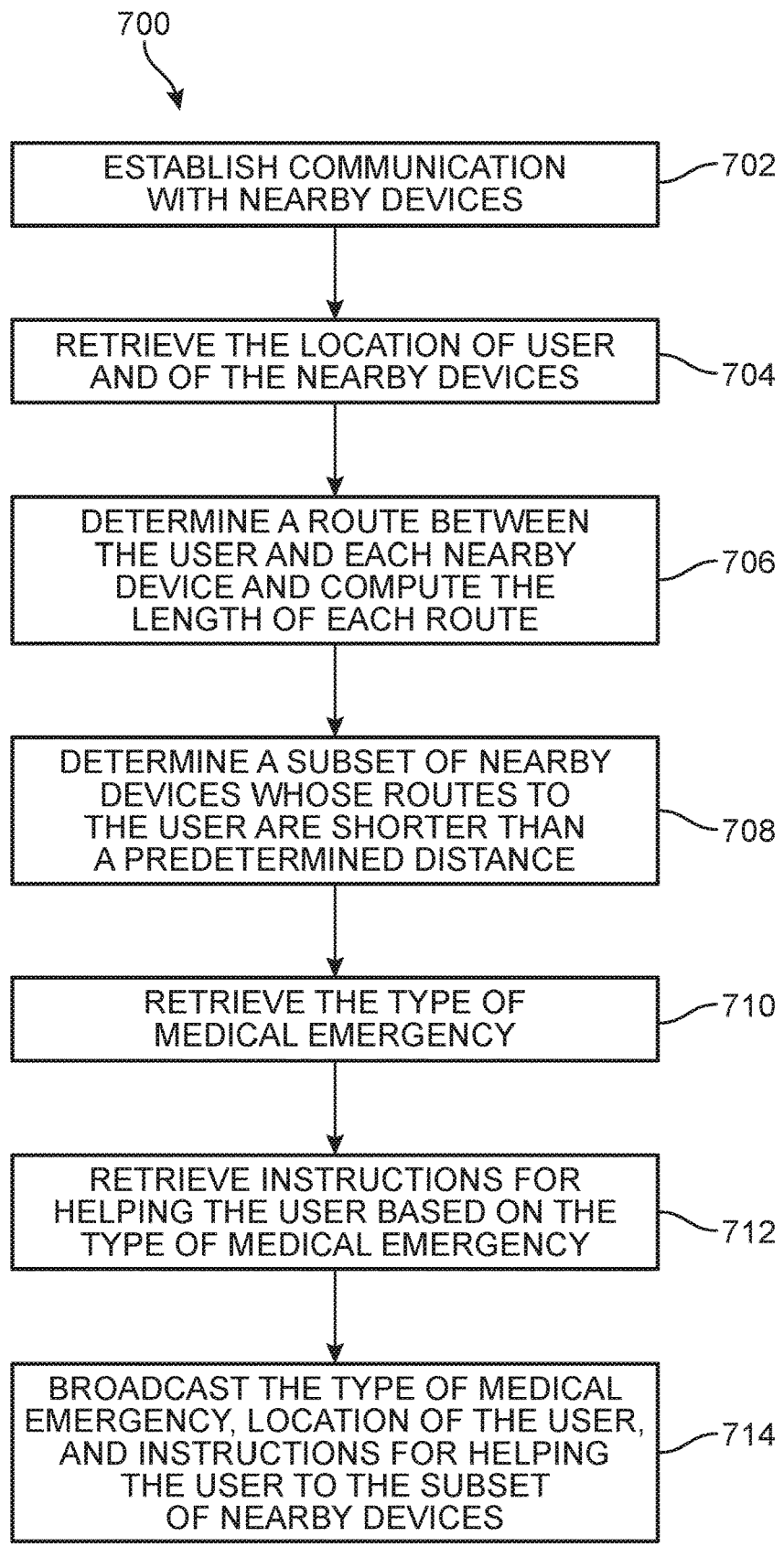
FIG. 7 is a schematic view of a method of broadcasting information about a medical emergency to a set of nearby devices, according to an embodiment.
Figure 8:
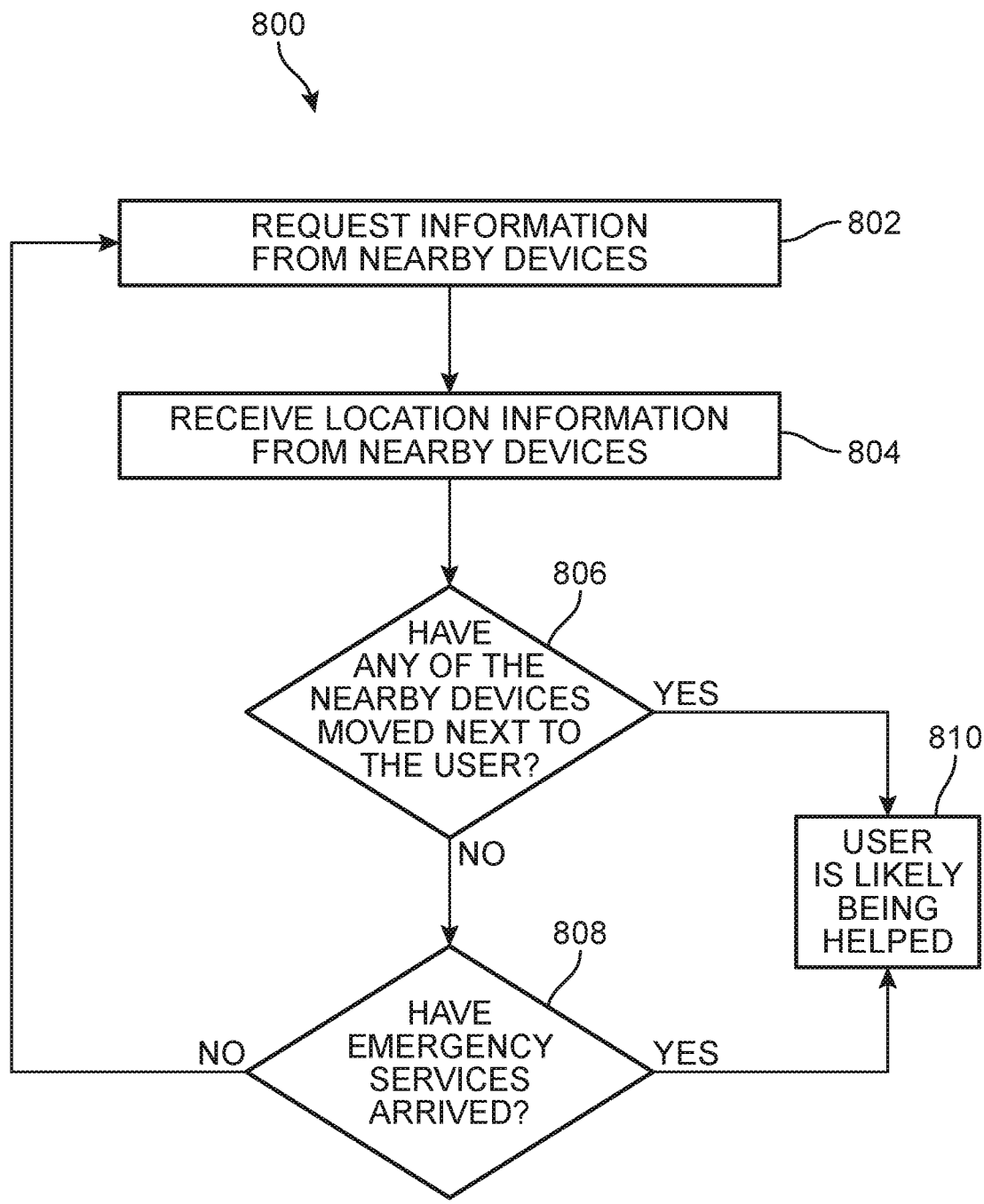
FIG. 8 is a schematic view of a method of confirming that a user has received assistance, according to an embodiment.

FIGS. 6-8 depict schematic views of various subprocesses that may be carried out as part of the overall process discussed above and shown in FIG. 1. In FIG. 6, a device (such as device 210) may carry out various steps of a process 600 to detect a medical emergency. Starting in step 602, device 210 may monitor information from one or more sensors. Next, in step 604, device 210 may identify a medical event. In step 606, device 210 may classify the medical event. In some cases, the medical event may be identified and/or classified using a machine learning algorithm. Examples of algorithms that could be used include clustering algorithms, decision trees, and neural networks.

Next, in step 608, device 210 may determine if the medical event is a medical emergency based on the classification performed in step 606. If so, device 210 may proceed to step 610. Otherwise, device 210 may return to step 602 to continue monitoring sensed information for any medical events.

In step 610, device 210 may prepare information about the medical emergency for broadcasting over a network to other nearby devices. The prepared information may include the type of medical emergency, the location of the user in need of assistance, and any instructions that may be provided to users who are able to provide assistance.

In FIG. 7, device 210 may carry out various steps of a process 700 to send information about a medical emergency to nearby devices (and users). In step 702, device 210 may establish communication with any nearby devices. In step 704, device 210 may retrieve the location of the user wearing/carrying device 210 as well as the locations of any nearby devices. Next, in step 706, device 210 may determine a route between the user and each nearby device. Device 210 may also compute the length of each route.

In step 708, device 210 may determine a subset of nearby devices whose routes to the user are shorter than a predetermined distance. By ensuring no devices are further than a predetermined distance, device 210 can prevent information about the medical emergency from being sent to users who are too far away and who would be unable to reach the user before emergency services personnel arrive.

In step 710 the type of medical emergency may be retrieved. For example, in a previous step the system could have determined that the type of medical emergency is heart attack, hypoglycemia, or an asthma attack. In step 712, device 210 may retrieve instructions for helping the user based on the type of medical emergency.

Finally, in step 714, device 210 may broadcast one or more of the type of medical emergency, the location of the assisted user, and any instructions for helping the assisted user. Specifically, this information may be broadcast to the subset of nearby devices determined in step 708.

In FIG. 8, device 210 may carry out various steps to confirm that a user has been assisted, thereby allowing the system to stop transmitting information requesting assistance. Starting in step 802, device 210 may request information from nearby devices. This request may include, at least, a request for location information from each device. In step 804, device 210 receives location information from one or more nearby devices. Next, in step 806, device 210 may determine, using the locations of each device, if any of the nearby devices have moved close to the user. If so, device 210 proceeds to step 810 and determines that the user is likely being helped. If not, device 210 proceeds to step 808. In this step, which is optional in some embodiments, device 210 can check whether emergency services have arrived. In some cases, for example, a device could receive a notification that emergency services have arrived. In that case, the device could register a request to receive a notification with the emergency services dispatch. If emergency services have arrived, device 210 proceeds to step 810. Otherwise, device 210 returns to step 802 to continue requesting information and monitoring whether any nearby devices move close to the user.

The provisions described above may also be used to trigger the exchange of medical information. For example, in some embodiments, upon determining that a medical emergency has occurred, a user device could send a request to have medical records for the user automatically delivered to emergency personnel and/or other medical providers (such as a doctor or hospital). This allows medical information to be shared before a user arrives at a doctor's office, hospital or other provider.

It may also be appreciated that in some embodiments, sensed data may be offloaded to a third party for analysis. For example, in some embodiments sensed data regarding a medical emergency could be transmitted to one or more cloud based systems over a network. The cloud based system may include an Artificial Intelligence (AI) that is trained to analyze medical information. After analyzing the sensed information, the AI could determine the type of medical emergency and/or provide instructions for assisting a user. This output can then be sent back to the user device for distribution to nearby devices and/or to medical providers.

The processes and methods of the embodiments described in this detailed description and shown in the figures can be implemented using any kind of computing system having one or more central processing units (CPUs) and/or graphics processing units (GPUs). The processes and methods of the embodiments could also be implemented using special purpose circuitry such as an application specific integrated circuit (ASIC). The processes and methods of the embodiments may also be implemented on computing systems including read only memory (ROM) and/or random access memory (RAM), which may be connected to one or more processing units. Examples of computing systems and devices include, but are not limited to: servers, cellular phones, smart phones, tablet computers, notebook computers, e-book readers, laptop or desktop computers, all-in-one computers, as well as various kinds of digital media players.

The processes and methods of the embodiments can be stored as instructions and/or data on non-transitory computer-readable media. The non-transitory computer readable medium may include any suitable computer readable medium, such as a memory, such as RAM, ROM, flash memory, or any other type of memory known in the art. In some embodiments, the non-transitory computer readable medium may include, for example, an electronic storage device, a magnetic storage device, an optical storage device, an electromagnetic storage device, a semiconductor storage device, or any suitable combination of such devices. More specific examples of the non-transitory computer readable medium may include a portable computer diskette, a floppy disk, a hard disk, magnetic disks or tapes, a read-only memory (ROM), a random access memory (RAM), a static random access memory (SRAM), a portable compact disc read-only memory (CD-ROM), an erasable programmable read-only memory (EPROM or Flash memory), electrically erasable programmable read-only memories (EEPROM), a digital versatile disk (DVD and DVD-ROM), a memory stick, other kinds of solid state drives, and any suitable combination of these exemplary media. A non-transitory computer readable medium, as used herein, is not to be construed as being transitory signals, such as radio waves or other freely propagating electromagnetic waves, electromagnetic waves propagating through a waveguide or other transmission media (e.g., light pulses passing through a fiber-optic cable), or electrical signals transmitted through a wire.

Instructions stored on the non-transitory computer readable medium for carrying out operations of the present invention may be instruction-set-architecture (ISA) instructions, assembler instructions, machine instructions, machine dependent instructions, microcode, firmware instructions, configuration data for integrated circuitry, state-setting data, or source code or object code written in any of one or more programming languages, including an object oriented programming language such as Smalltalk, C++, or suitable language, and procedural programming languages, such as the "C" programming language or similar programming languages.

Aspects of the present disclosure are described in association with figures illustrating flowcharts and/or block diagrams of methods, apparatus (systems), and computing products. It will be understood that each block of the flowcharts and/or block diagrams can be implemented by computer readable instructions. The flowcharts and block diagrams in the figures illustrate the architecture, functionality, and operation of possible implementations of various disclosed embodiments. Accordingly, each block in the flowchart or block diagrams may represent a module, segment, or portion of instructions. In some implementations, the functions set forth in the figures and claims may occur in an alternative order than listed and/or illustrated.

The embodiments may utilize any kind of network for communication between separate computing systems. A network can comprise any combination of local area networks (LANs) and/or wide area networks (WANs), using both wired and wireless communication systems. A network may use various known communications technologies and/or protocols. Communication technologies can include, but are not limited to: Ethernet, 802.11, worldwide interoperability for microwave access (WiMAX), mobile broadband (such as CDMA, and LTE), digital subscriber line (DSL), cable internet access, satellite broadband, wireless ISP, fiber optic internet, as well as other wired and wireless technologies. Networking protocols used on a network may include transmission control protocol/Internet protocol (TCP/IP), multiprotocol label switching (MPLS), User Datagram Protocol (UDP), hypertext transport protocol (HTTP), hypertext transport protocol secure (HTTPS) and file transfer protocol (FTP) as well as other protocols.

Data exchanged over a network may be represented using technologies and/or formats including hypertext markup language (HTML), extensible markup language (XML), Atom, JavaScript Object Notation (JSON), YAML, as well as other data exchange formats. In addition, information transferred over a network can be encrypted using conventional encryption technologies such as secure sockets layer (SSL), transport layer security (TLS), and Internet Protocol security (Ipsec).

While various embodiments of the invention have been described, the description is intended to be exemplary, rather than limiting, and it will be apparent to those of ordinary skill in the art that many more embodiments and implementations are possible that are within the scope of the invention. Accordingly, the invention is not to be restricted except in light of the attached claims and their equivalents. Also, various modifications and changes may be made within the scope of the attached claims.

We claim:

1. A method of requesting assistance for a user experiencing a medical emergency, comprising:
   receiving sensed information from a sensor disposed in a user device associated with the user;
   determining that the user is experiencing a medical emergency based on the sensed information, by:
      identifying a medical event;
      classifying the medical event, using at least one of a clustering algorithm, a decision tree or a neural network; and
      determining, on the basis of the classification that the medical event is a medical emergency;
   establishing communication with one or more nearby devices;
   automatically sending information associated with the medical emergency to the one or more nearby devices; and
   monitoring a location of at least one nearby device of the one or more nearby devices and confirming that the at least one nearby device has moved near the user.

2. The method according to claim 1, wherein the user device is a smart watch.

3. The method according to claim 1, wherein the sensed information includes heart rate information.

4. The method according to claim 1, wherein the sensed information includes blood glucose level information.

5. The method according to claim 1, wherein the method further includes classifying the medical emergency to determine a type of medical emergency.

6. The method according to claim 5, wherein the information associated with the medical emergency includes the type of medical emergency and a location of the user device.

7. The method according to claim 6, wherein the information associated with the medical emergency further includes instructions for assisting the user.

8. A method of requesting assistance for a user experiencing a medical emergency, comprising:
registering a request for notifications from an emergency dispatcher;
determining that a user is experiencing a medical emergency;
sending a message to the emergency dispatcher indicating that the user is experiencing the medical emergency;
transmitting information requesting assistance for the user to nearby devices by:
establishing communication with a nearby device;
retrieving a location for the nearby device;
determining a route between the user and the nearby device;
calculating a route length for the route;
retrieving a predetermined distance; and
sending information about the medical emergency to the nearby device if the route length is less than or equal to the predetermined distance;
confirming that the user has been assisted by:
monitoring the location of the nearby device;
determining if the nearby device has moved close enough to the user to provide assistance;
checking for notifications from the emergency dispatcher;
wherein upon determining that (i) the nearby device has moved close enough to the user to provide assistance, or (ii) receiving a notification indicating that emergency services have arrived to provide assistance to the user, the method comprises stopping transmitting information requesting assistance; and
continuing transmitting information requesting assistance otherwise.

9. The method according to claim 8, wherein establishing communication with the nearby device includes communicating with the nearby device over a personal area network.

10. The method according to claim 8, wherein establishing communication with the nearby device includes communicating with the nearby device over a local area network.

11. The method according to claim 8, wherein establishing communication with the nearby device includes communicating with the nearby device over a wide area network.

12. The method according to claim 8, wherein the method further includes sending instructions for assisting the user to the nearby device.

13. A user device, comprising:
one or more processors;
memory configured to store instructions that are executable by the one or more processors to:
register a request for notifications from an emergency dispatcher;
determine that a user is experiencing a medical emergency;
send a message to the emergency dispatcher indicating that the user is experiencing the medical emergency;
transmit information requesting assistance for the user to nearby devices by:
establishing communication with a nearby device;
retrieving a location for the nearby device;
determining a route between the user and the nearby device;
calculating a route length for the route;
retrieving a predetermined distance; and
sending information about the medical emergency to the nearby device if the route length is less than or equal to the predetermined distance;
confirm that the user has been assisted by:
monitoring the location of the nearby device;
determining if the nearby device has moved close enough to the user to provide assistance;
checking for notifications from the emergency dispatcher;
wherein upon determining that (i) the nearby device has moved close enough to the user to provide assistance, or (ii) receiving a notification indicating that emergency services have arrived to provide assistance to the user, stopping transmitting information requesting assistance; and
continuing transmitting information requesting assistance otherwise.

14. The user device according to claim 13, wherein the user device further includes a sensor, and wherein the instructions are further executable to determine that a user is experiencing a medical emergency by analyzing information received from the sensor.

15. The user device according to claim 14, wherein the sensor is an oximetry sensor.

16. The user device according to claim 14, wherein the sensor is a respiration sensor.

17. The user device according to claim 14, wherein the sensor is a skin conductance sensor.

18. The user device according to claim 14, wherein the sensor is a blood glucose sensor.

19. The user device according to claim 14, wherein the sensor is an accelerometer.

* * * * *